(12) United States Patent
Blakley et al.

(10) Patent No.: US 7,814,324 B2
(45) Date of Patent: *Oct. 12, 2010

(54) METHOD OF MAKING A PATIENT MONITOR

(75) Inventors: Daniel R. Blakley, Philomath, OR (US); John S. Dunfield, Corvallis, OR (US); Steven J. Simske, Fort Collins, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1632 days.

This patent is subject to a terminal disclaimer.

(21) Appl. No.: 11/064,866

(22) Filed: Feb. 24, 2005

(65) Prior Publication Data

US 2006/0189924 A1 Aug. 24, 2006

(51) Int. Cl.
*H04L 9/32* (2006.01)
(52) U.S. Cl. .................................. 713/176; 340/539.12
(58) Field of Classification Search ........................ None
See application file for complete search history.

(56) References Cited

U.S. PATENT DOCUMENTS

| | | | |
|---|---|---|---|
| 5,620,473 A | 4/1997 | Poore | |
| 5,701,894 A | 12/1997 | Cherry et al. | |
| 5,817,137 A | 10/1998 | Kaemmerer | |
| 5,867,821 A * | 2/1999 | Ballantyne et al. | 705/2 |
| 5,960,085 A * | 9/1999 | de la Huerga | 340/5.61 |
| 6,285,909 B1 | 9/2001 | Sweeney et al. | |
| 6,287,252 B1 * | 9/2001 | Lugo | 600/300 |
| 6,312,378 B1 | 11/2001 | Bardy | |
| 6,358,203 B2 | 3/2002 | Bardy | |
| 6,398,727 B1 * | 6/2002 | Bui et al. | 600/300 |
| 6,454,708 B1 | 9/2002 | Ferguson et al. | |
| 6,544,174 B2 * | 4/2003 | West et al. | 600/300 |
| 6,607,485 B2 | 8/2003 | Bardy | |
| 7,310,734 B2 * | 12/2007 | Boate et al. | 713/186 |
| 2003/0088292 A1 | 5/2003 | Anderson et al. | |
| 2003/0181818 A1 | 9/2003 | Kim et al. | |

* cited by examiner

*Primary Examiner*—Pramila Parthasarathy

(57) ABSTRACT

A method for making a patient monitor includes providing an electronic device operatively connected to the monitor. The device is configured to measure predetermined signals from a user and to generate therefrom a substantially unique signature specific to the user. The method further includes storing the signature in the electronic device. The electronic device is adapted to compare newly acquired signatures to the substantially unique signature, and to recognize at least one difference from the substantially unique signature. Recognition of a difference in the signatures signifies a new user, whereupon the electronic device acquires new predetermined signals and generates therefrom a new substantially unique signature specific to the new user.

53 Claims, 1 Drawing Sheet

METHOD OF MAKING A PATIENT MONITOR

BACKGROUND

The present disclosure relates generally to patient monitors.

Patient monitors, for example, cardiac monitors (ambulatory or stationary), allow a medical care provider to monitor a patient's condition, either remotely or within the patient's proximity. Currently, patients or medical care providers input patient-specific information into patient monitors prior to initiating patient care and/or patient use. The input information allows the medical care provider to keep the information and records obtained from the monitor matched with the correct patient's information. In order to substantially avoid misapplication or confusion of the patient data obtained from the monitor, a medical care provider generally should be informed that a new user has begun wearing the monitor.

Further, a patient may change the position and/or configuration of the monitor. After such a change, the monitor may indicate a transition point, which may affect downstream analysis of the patient data, potential alarm limits or indications, and possibly patient diagnosis. In such instances, a patient may be prompted to reenter patient-specific information and/or disable alarms.

As such, it would be desirable to provide a patient monitor that is capable of distinguishing between users without having to input patient specific information for the new user. It would also be desirable to provide a patient monitor that is capable of adjusting for an altered configuration(s) of the same user.

SUMMARY

A method for making a patient monitor is disclosed. The method includes providing an electronic device operatively connected to the monitor. The electronic device is configured to measure predetermined signals from a user and to generate therefrom a substantially unique signature specific to the user. The method further includes storing the substantially unique signature in the electronic device. The electronic device is adapted to compare newly acquired signatures to the substantially unique signature, and to recognize at least one difference from the substantially unique signature. Recognition of a difference in the signatures signifies a new user, whereupon the electronic device acquires new predetermined signals and generates therefrom a new substantially unique signature specific to the new user.

BRIEF DESCRIPTION OF THE DRAWINGS

Objects, features and advantages will become apparent by reference to the following detailed description and drawings, in which like reference numerals correspond to similar, though not necessarily identical components. For the sake of brevity, reference numerals having a previously described function may not necessarily be described in connection with subsequent drawings in which they appear.

DETAILED DESCRIPTION

The present disclosure relates to patient monitors, and methods of making the same, that are capable of distinguishing between different users or recognizing the same user having a new configuration and/or connection to the monitor. Further, embodiment(s) of the patient monitors may reset upon recognition of a new user, such that the new user may use the monitor without having to input information specific to himself or herself. Still further, embodiment(s) of the patient monitor may compress, tokenize, and/or template predetermined signals from the user into a signature specific to that user, thus achieving substantial storage capabilities. It is to be understood that embodiment(s) of the present disclosure may be useful with any set of patient and/or environmental monitors that are simultaneously monitored and can form a signature.

Further, it is to be understood that the term "signature" as referred to herein may include a signature confidence value that is based on predetermined signals specific to a particular patient.

Figure 1:
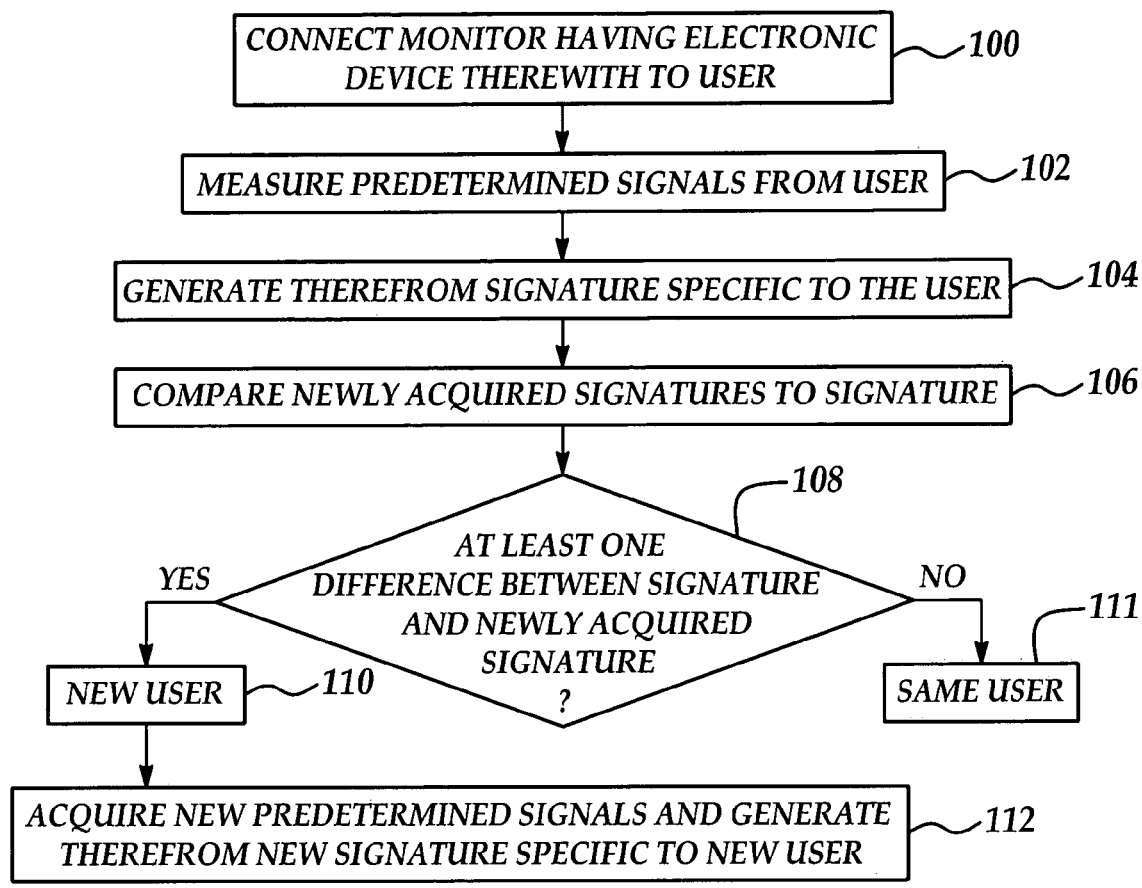
FIG. 1 is a flow diagram depicting an embodiment of a method of the present disclosure.

Referring now to FIG. 1, a method for making a patient monitor according to embodiment(s) of the present disclosure is depicted in a flow diagram. The method includes providing an electronic device operatively connected to the monitor and to the user, as depicted at 100. The device is adapted to measure predetermined signals from the user, as depicted at 102. A substantially unique signature specific to the user is generated from the predetermined signals, as depicted at 104; and the electronic device is configured to store the signature in the electronic device. The electronic device is adapted to compare newly acquired signatures to the substantially unique signature, as depicted at 106, and to recognize, in some instances, at least one difference between the substantially unique signature and the newly acquired signatures, as depicted at 108. If there is at least one difference/significant difference, this may signify a new user, as depicted at 110, whereupon the electronic device acquires new predetermined signals and generates therefrom a new substantially unique signature specific to the new user, as depicted at 112. Moreover, as more unique signal differences are compared and cross-correlated, meta-metrics may substantially improve the ability to distinguish between signatures due, at least in part, to the substantiation of acquired data from the predetermined signals. If the substantially unique signature is substantially similar to the newly acquired signature, this signifies the same user, as depicted at 111. In an embodiment in which the same user is recognized, the newly acquired signals may be transformed into the previously stored substantially unique signature, or the extant signature may be updated (forward transformed), for example, to correspond to a new monitor configuration for the same user.

The terms "difference" and "significant difference" as referred to herein are defined to mean values that are outside the range of a stored signature, discontinuity in the data from the predetermined signals, the data from the predetermined signals substantially matches (or is more consistent with) another signature, and/or combinations thereof.

Figure 2:
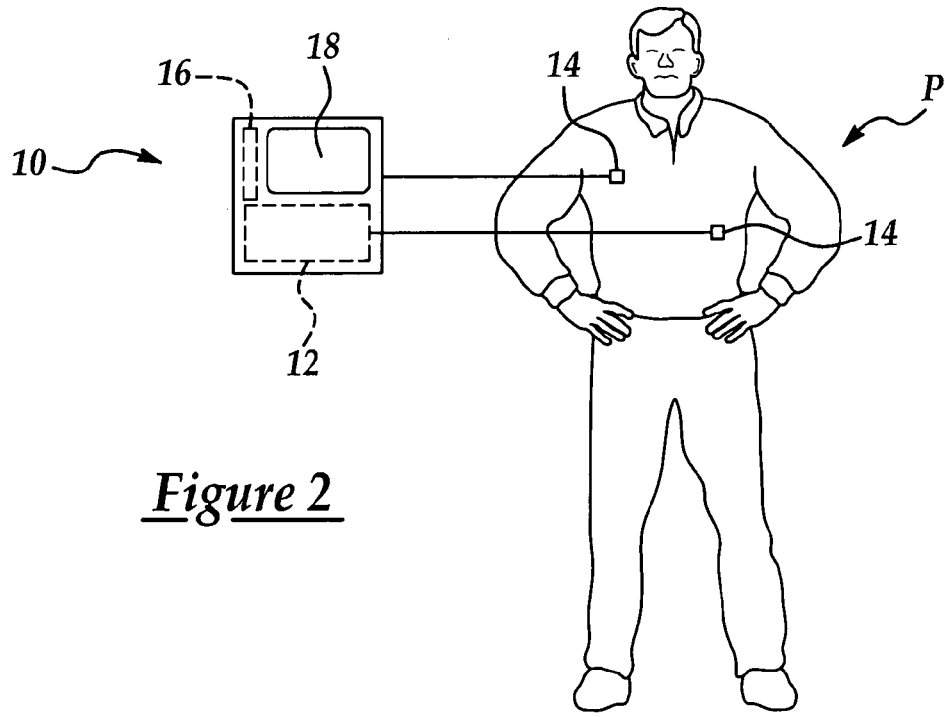
FIG. 2 is a schematic diagram showing an embodiment of the monitor connected to a patient.

Referring now to FIG. 2, an embodiment of making a patient monitor 10 includes providing an electronic device 12 operatively connected to/within the monitor 10. Non-limitative examples of suitable electronic devices include volume and velocity recorders, ECG monitors, breathing sensors (a non-limitative example of which includes a piezoelectric sensor), accelerometers, temperature sensors, pH sensors, other transcutaneous sensors, and the like, and/or combinations thereof.

In an embodiment, the electronic device 12 may measure predetermined signals from a user/patient P and generate therefrom a substantially unique signature specific to the user P. In a non-limitative example, the predetermined signals include measurements of cardiac activity or cardiac signals. Other non-limiting examples of the predetermined signals that may be measured by the electronic device include, but are not limited to respiration rate, body temperature, electrocardiogram waveforms, transformed vectorcardiograms waveforms, vectorcardiogram waveforms, heart sounds, accelerometer measurements, physiological measurements, blood pressure, aortic ejection velocity, fingerprint scans, retinal scans, atomic clock data, positional data (a non-limiting example of which includes data from a Global Positioning System (GPS)), voice analysis, data from a microfluidic device, weight, hemoglobin counts, blood oxygen levels, and combinations thereof. It is to be understood that the predetermined signals may be digital signals, analog signals, and/or combinations thereof.

It is to be understood that the electronic device 12 may have electrodes or leads 14 operatively connected thereto. The electrodes/leads 14 may be capable of receiving and transmitting such signals from the user P to the electronic device 12. The monitor 10 may further optionally include a display 18 operatively connected thereto.

The electronic device 12 may also include an electronic storage member 16 that is capable of storing the substantially unique signature (a non-limiting examples of which is a first signature) of the user P therein. It is to be understood that signal compression based on the user's signature may be used such that substantially the maximum amount of storage may be achieved. In an embodiment, the electronic device 12 templates or "signatures" the raw data generated from the predetermined signals. The electronic device 12 is capable of replacing the raw data with the signature and/or a set of signatures.

Without being bound to any theory, it is believed that the predetermined signals are unique to the particular user P, and therefore may be used to calculate a signature that is substantially unique and specific to that user P. Further, it is believed that each user P has a substantially fixed physiology such that their predetermined signals remain substantially similar, thus allowing the signature to be substantially unique to that user P.

In an embodiment, the signature includes a character or a combination of two or more characters. It is to be understood that each character may be a linear or non-linear combination of numerical values or ranges that correspond to one of the predetermined signal(s).

Examples of the numerical values or ranges that may be derived from the predetermined signals, and used to determined the character(s), include unconditional (primary) sensitivity value(s)/range(s), conditional (secondary) sensitivity value(s)/range(s), multi-level conditional sensitivity value(s)/range(s), and/or combinations thereof. The values/ranges may be based on, for example, information from a user's electrocardiogram reading.

A non-limiting example of an unconditional (primary) sensitivity value(s)/range(s) is a resting heart rate ranging between about 60 bpm and about 88 bpm. An example of a conditional (secondary) sensitivity value(s)/range(s) is an ST/TP interval ratio ranging between about 0.4 and about 0.6 when the heart rate ranges between about 60 bpm and about 90 bpm. An example of a multi-level conditional sensitivity value(s)/range(s) is a vectorcardiogram with a mean axis of about 75+/−12 at a heart rate ranging between about 60 bpm and about 90 bpm, about 77+/−8 at a heart rate ranging between about 90 bpm and about 120 bpm, and a prominent third heart sound occurring between about 0.25 and about 0.5 of diastole (i.e. TP interval).

As previously indicated, the numerical values/ranges of the predetermined signal(s) may be linearly or non-linearly combined to determine the character for the particular signal. A non-limitative example of a non-linear combination is one based on, for example Gaussian fits, direct probability curves, weighted multiple non-linear regression analysis, neural network analysis, and/or the like.

Further, the data corresponding to the predetermined signals for an individual user may be classified and compared to a population of patients/users using principal component analysis (PCA), support vector machines (SVM), or the like. It is to be understood that with these techniques, identification of a unique user is generally by comparison with a greater population of values of such a nature that the signature of a specific user is substantially unique.

In an embodiment, the character for a particular predetermined signal may be based on a combination of the numerical value/range and a predetermined value for a user population. For example, the character may be based on weighting how close each signal measurement is to the center/mean of the user's range (a non-limiting example of which is centered on the mean and based on the predetermined signal measurements), and multiplying the weight by the relative value of a measurement for the overall user population (i.e. the predictive value). In an embodiment, the following equation may be used to calculate the user's character:

$$A*B \quad \text{(Equation 1)}$$

where A=weighted value or (absolute value of(user value for a predetermined signal−mean of user's range))/(range width/2) and B=predictive value of the specific signal's overall population.

A non-limiting example using the previously described equation to determine a user's character(s) is as follows. User A has a resting heart rate at 78 bpm. The character calculated by the electronic device 12 may be based on any predetermined signal, and for User A the predetermined signal is heart rate. The numerical range based on User A's heart rate is 75 bpm-87 bpm. Equation A results in a weight value of 50% when User A's information is plugged into the equation: |(78−81)|/((87−75)/2)=0.5 using a linear fit. It is to be understood that a Gaussian fit, an empirically-derived curve fit, and other like "fits" (including, but not limited to those mentioned hereinabove) may be used to determine the character(s) based on the predetermined signal numerical values/ranges. In this example, the predictive value of the specific signal (in this example, heart rate) is 0.3, resulting in User A having a heart rate character of 0.5*0.3=0.15.

In another non-limiting example, User B also has a resting heart rate at 78 bpm. User B's heart rate range is 76 bpm to 88 bpm. Plugging User B's values into the equation results in a weight (part A of equation 1) of |(78−82)|/((88−76)/2)=0.33, which when multiplied by the same predictive value (B=0.3), gives a lower overall character of 0.11.

The sum of the characters (i.e. the calculated A*B values for each measured predetermined signal) for a user gives the user's identifying, substantially unique signature (i.e. signature confidence value). The signature may be used to identify that user among several other users, as it is derived from the user's unique set of characters, which is based on the user's predetermined signals.

In an embodiment, the electronic device 12 may calculate characters every few minutes to determine if the rate remains constant or if it changes, whereby a change signifies the new user. An example summation of the overall characters in an interval indicating a user change may look like the following:

23.5, 25.4, 27.7, 13.2, 14.5, 12.7 .... This sequence indicates a first user P having a signature range of 25.5+/−2.0 and a second user P having a signature range of 13.5+/−0.9. The electronic device 12 recognizes a change in the rates, or a transition point, and thus acquires new signals and builds a new substantially unique signature specific to the new user. In this example, the average of the new user is reduced. Edge determination algorithms (a non-limitative example of which includes measuring variance (z-metric) values to both sides of putative transitions) may be used to determine the transition point of the interval.

Upon receiving additional predetermined signals, the electronic device 12 derives another signature (a non-limitative example of which is a second signature) based on the newly acquired predetermined signals. The electronic device 12 is capable of comparing the previously stored substantially unique first signature with the newly acquired second signature. If the previously stored first signature substantially matches the newly acquired second signature, the electronic device 12 recognizes that the user P is the same user and continues to take such signal measurements. Further, if the electronic device 12 recognizes the same user, it may transform the newly acquired second signature to the first signature, or may update the previously stored signature, thereby adjusting for any variations that may result from the electronic device 12 having a new configuration or connection to the patient P. If desired, the first signature may be kept if the same user is recognized, and/or the first signature may be kept in storage/archive.

However, if the previously stored first signature is different from the newly acquired second signature, the electronic device 12 recognizes this difference and attributes the difference to a new user P. Upon determining that the monitor 10 has a new user P, the electronic device 12 goes into an "acquire and build" mode where it acquires more predetermined signals, generates therefrom a new substantially unique signature specific to the new user P, and replaces the previously stored signature with the new signature for future comparisons.

It is to be understood that the electronic device 12 may continue to measure signals, determine numerical ranges, calculate characters and form signatures based thereon, and to compare the data with previously stored data to monitor who is using the patient monitor 10.

In an embodiment, the electronic device 12 may detect a lapse between the measurements of the predetermined signals (a non-limitative example of which is a measurement of cardiac activity to non-cardiac activity and back to cardiac activity in a cardiac monitor). After such a lapse, the electronic device 12 acquires new predetermined signals and builds, as described herein, a signature therefrom. In order to determine whether the current user P is a new user P, the electronic device 12 compares the new signature with the most recently stored signature. If the signatures substantially match, the electronic device 12 continues to measure signals from the user P or transforms the new signature to the previously stored signature. If, however, the signatures are different, the electronic device 12 acquires additional signals, builds a new signature based on those signals, and stores the new signature such that the monitor 10 is reset for the new user P.

It is to be understood that user/patient P may be any patient, including but not limited to humans, test dummies, synthetic humans, animals, and/or the like.

Advantages of embodiment(s) of the patient monitor 10 include, but are not limited to the following. Embodiment(s) of the method are capable of distinguishing between different users, or recognizing the same user, of the patient monitor 10. Further, embodiment(s) of the patient monitors 10 may reset upon recognition of a new user, such that the new user may use the monitor 10 without having to input information specific to himself or herself. Still further, embodiment(s) of the patient monitor 10 may template signals from the user P into a signature specific to that user, thus achieving substantial storage capabilities without retaining all of the collected data.

While several embodiments have been described in detail, it will be apparent to those skilled in the art that the disclosed embodiments may be modified. Therefore, the foregoing description is to be considered exemplary rather than limiting.

What is claimed is:

1. A method for making a patient monitor, comprising:
providing an electronic device operatively connected to the patient monitor the device adapted to measure predetermined signals from a user and generate therefrom a substantially unique signature specific to the user, the substantially unique signature including a signature confidence value that is based on the predetermined signals; and
configuring the electronic device to store the signature;
wherein the electronic device is adapted to compare newly acquired signatures to the substantially unique signature, and to recognize at least one difference from the substantially unique signature, thereby signifying a new user, whereupon the electronic device acquires new predetermined signals and generates therefrom a new substantially unique signature specific to the new user.

2. The method as defined in claim 1 wherein at least one of the substantially unique signature and the new substantially unique signature comprise at least one character.

3. The method as defined in claim 2 wherein the at least one character is derived from at least one of a linear combination and a non-linear combination of the predetermined signals.

4. The method as defined in claim 3 wherein the at least one of the linear combination and the non-linear combination of the predetermined signals is based on at least one of a numerical value and a numerical range derived from the predetermined signals.

5. The method as defined in claim 2 wherein at least one of a numerical value and a numerical range is derived from the predetermined signals, and the at least one character is generated from a combination of the at least one of the numerical value and the numerical range and a predetermined value for a user population.

6. The method as defined in claim 1 wherein the predetermined signals comprise at least one of respiration rate, body temperature, electrocardiogram waveforms, transformed vectorcardiograms waveforms, vectorcardiogram waveforms, heart sounds, accelerometer measurements, physiological measurements, blood pressure, aortic ejection velocity, fingerprint scans, retinal scans, atomic clock data, positional data, voice analysis, data from a microfluidic device, weight, hemoglobin counts, blood oxygen levels, and combinations thereof.

7. The method as defined in claim 1 wherein at least one of unconditional sensitivity values, conditional sensitivity values, and multi-level conditional sensitivity values are derived from the predetermined signals.

8. The method as defined in claim 7 wherein the at least one of unconditional sensitivity values, conditional sensitivity values, and multi-level conditional sensitivity values are at least one of a numerical value and a numerical range.

9. The method as defined in claim 1 wherein the electronic device includes at least two electrodes operatively connected thereto, the at least two electrodes adapted to receive the predetermined signals from at least one of the user and the new user.

10. The method as defined in claim 1 wherein the predetermined signals are at least one of digital signals, analog signals, and combinations thereof.

11. The method as defined in claim 1 wherein the electronic device is configured to template the predetermined signals for signal compression.

12. A patient monitor, comprising: an electronic device operatively connected to the patient monitor, the device adapted to measure predetermined signals from a user and to generate therefrom a substantially unique signature specific to the user, the substantially unique signature including a signature confidence value that is based on the predetermined signals; and
    an electronic storage member operatively connected to the electronic device, the electronic storage member adapted to store the substantially unique signature;
    wherein the electronic device is adapted to compare newly acquired signatures to the substantially unique signature, and to recognize at least one difference from the substantially unique signature, thereby signifying a new user, whereupon the electronic device acquires new predetermined signals and generates therefrom a new substantially unique signature specific to the new user.

13. The patient monitor as defined in claim 1 wherein at least one of the substantially unique signature and the new substantially unique signature comprise at least one character.

14. The patient monitor as defined in claim 13 wherein the at least one character is derived from at least one of a linear combination and a non-linear combination of the predetermined signals.

15. The patient monitor as defined in claim 14 wherein the at least one of the linear combination and the non-linear combination of the predetermined signals is based on at least one of a numerical value and a numerical range derived from the predetermined signals.

16. The patient monitor as defined in claim 13 wherein at least one of a numerical value and a numerical range is derived from the predetermined signals, and wherein the at least one character is generated from a combination of the at least one of the numerical value and the numerical range and a predetermined value for a user population.

17. The patient monitor as defined in claim 12 wherein the predetermined signals comprise at least one of respiration rate, body temperature, electrocardiogram waveforms, transformed vectorcardiograms waveforms, vectorcardiogram waveforms, heart sounds, accelerometer measurements, physiological measurements, blood pressure, aortic ejection velocity, fingerprint scans, retinal scans, atomic clock data, positional data, voice analysis, data from a microfluidic device, weight, hemoglobin counts, blood oxygen levels, and combinations thereof.

18. The patient monitor as defined in claim 12 wherein at least one of unconditional sensitivity values, conditional sensitivity values, and multi-level conditional sensitivity values are derived from the predetermined signals.

19. The patient monitor as defined in claim 18 wherein the at least one of unconditional sensitivity values, conditional sensitivity values, and multi-level conditional sensitivity values are at least one of a numerical value and a numerical range.

20. The patient monitor as defined in claim 12 wherein the electronic device includes at least two electrodes operatively connected thereto, the at least two electrodes adapted to receive the predetermined signals from at least one of the user and the new user.

21. The patient monitor as defined in claim 12 wherein the predetermined signals are at least one of digital signals, analog signals, and combinations thereof.

22. The patient monitor as defined in claim 12 wherein the electronic device is adapted to template the predetermined signals for signal compression.

23. A system for recognizing a new user of a cardiac monitor, the system comprising: an electronic device operatively connected to the cardiac monitor, the device adapted to measure predetermined cardiac signals from a user and to generate therefrom a substantially unique signature specific to the user, the substantially unique signature including a signature confidence value that is based on the predetermined cardiac signals; and
    an electronic storage member operatively connected to the electronic device, the electronic storage member adapted to store the signature;
    wherein the electronic device is adapted to compare newly acquired signatures to the substantially unique signature, and to recognize at least one significant difference from the substantially unique signature, thereby signifying the new user, whereupon the electronic device acquires new predetermined cardiac signals and generates therefrom a new substantially unique signature specific to the new user.

24. The system as defined in claim 23 wherein the predetermined cardiac signals comprise at least one of electrocardiogram waveforms, transformed vectorcardiograms waveforms, vectorcardiogram waveforms, heart sounds, accelerometer measurements, physiological measurements, blood pressure, aortic ejection velocity, and combinations thereof.

25. The system as defined in claim 23 wherein at least one of the substantially unique signature and the new substantially unique signature comprise at least one character.

26. The system as defined in claim 25 wherein the at least one character is derived from at least one of a linear combination and a non-linear combination of the predetermined cardiac signals.

27. The system as defined in claim 26 wherein the at least one of the linear combination and the non-linear combination of the predetermined cardiac signals is based on at least one of a numerical value and a numerical range derived from the predetermined cardiac signals.

28. The system as defined in claim 25 wherein at least one of a numerical value and a numerical range is derived from the predetermined cardiac signals, and the at least one character is generated from a combination of the at least one of the numerical value and the numerical range and a predetermined value for a user population.

29. The system as defined in claim 23 wherein at least one of unconditional sensitivity values, conditional sensitivity values, and multi-level conditional sensitivity values are derived from the predetermined cardiac signals.

30. The system as defined in claim 29 wherein the at least one of unconditional sensitivity values, conditional sensitivity values, and multi-level conditional sensitivity values are at least one of a numerical value and a numerical range.

31. The system as defined in claim 23 wherein the electronic device includes at least two electrodes operatively connected thereto, the at least two electrodes adapted to receive the predetermined cardiac signals from at least one of the user and the new user.

32. The system as defined in claim 23 wherein the predetermined cardiac signals are at least one of digital signals, analog signals, and combinations thereof.

33. The system as defined in claim 23 wherein the electronic device is configured to template the predetermined cardiac signals for signal compression.

34. A method for differentiating between a user and a new user of a patient monitor, the method comprising:
measuring predetermined signals from the user;
from the predetermined signals of the user, generating a substantially unique first signature of the user, the substantially unique first signature including a signature confidence value that is based on the predetermined signals of the user;
measuring predetermined signals from a then-current user of the patient monitor;
from the predetermined signals of the then-current user, generating a second signature including a signature confidence value that is based on the predetermined signals of the then-current user; and
comparing the substantially unique first signature and the second signature to determine if the second signature substantially matches the substantially unique first signature;
wherein substantially similar first and second signatures indicate that the then-current user is the user and wherein different first and second signatures indicate that the then-current user is the new user.

35. The method as defined in claim 34 wherein generating the first and second signatures is accomplished by an electronic device that is adapted to measure the predetermined signals from at least one of the user and the then-current user, and generate from the predetermined signals the first and second signatures.

36. The method as defined in claim 35 wherein the electronic device stores the substantially unique first signature therein and is adapted to compare the second signature to the substantially unique first signature and to at least one of distinguish between the user and the new user and to recognize the user.

37. The method as defined in claim 34 wherein generating at least one of the first and second signatures is accomplished by measuring the predetermined signals of at least one of the user and the then-current user, respectively, and deriving at least one character from the predetermined signals of at least one of the user and the then-current user.

38. The method as defined in claim 37 wherein the at least one character is at least one of a linear combination and a non-linear combination of the predetermined signals of at least one of the user and the then-current user.

39. The method as defined in claim 38 wherein the at least one of the linear combination and the non-linear combination of the predetermined signals of at least one of the user and the then-current user is based on at least one of a numerical value and a numerical range derived from the predetermined signals of at least one of the user and the then-current user.

40. The method as defined in claim 37 wherein at least one of a numerical value and a numerical range is derived from the predetermined signals of at least one of the user and the then-current user, and the at least one character is generated from a combination of the at least one of the numerical value and the numerical range and a predetermined value for a user population.

41. The method as defined in claim 35 wherein the predetermined signals of at least one of the user and the then-current user comprise at least one of respiration rate, body temperature, electrocardiogram waveforms, transformed vectorcardiograms waveforms, vectorcardiogram waveforms, heart sounds, accelerometer measurements, physiological measurements, blood pressure, aortic ejection velocity, fingerprint scans, retinal scans, atomic clock data, positional data, voice analysis, data from a microfluidic device, weight, hemoglobin counts, blood oxygen levels, and combinations thereof.

42. The method as defined in claim 34 wherein at least one of unconditional sensitivity values, conditional sensitivity values, and multi-level conditional sensitivity values are derived from the predetermined signals of at least one of the user and the then-current user.

43. A method for monitoring a user's identity, the method comprising: generating a substantially unique first signature of the user, the substantially unique signature including a signature confidence value that is based on measurements of predetermined signals;
recognizing a lapse in predetermined signal measurements;
generating a second signature, the second signature including a signature confidence value that is based on measurements of predetermined signals taken after the lapse; and
comparing the substantially unique first signature and the second signature to determine if the second signature substantially matches the substantially unique first signature;
wherein substantially similar first and second signatures identify the user and wherein different first and second signatures identify a new user,
wherein generating the first and second signatures is accomplished by an electronic device that is adapted to measure predetermined signals from at least one of the user and the new user, and generate from the predetermined signals of the first and second signatures.

44. The method as defined in claim 43 wherein the electronic device stores the substantially unique first signature therein and is adapted to compare the second signature to the substantially unique first signature and to at least one of distinguish between the user and the new user and to recognize the user.

45. The method as defined in claim 43 wherein generating at least one of the first and second signatures is accomplished by measuring predetermined signals, and deriving at least one character from the predetermined signals.

46. The method as defined in claim 45 wherein the at least one character is at least one of a linear combination and a non-linear combination of the predetermined signals.

47. The method as defined in claim 46 wherein the at least one of the linear combination and the non-linear combination of the predetermined signals is based on at least one of a numerical value and a numerical range derived from the predetermined signals.

48. The method as defined in claim 45 wherein at least one of unconditional sensitivity values, conditional sensitivity values, and multi-level conditional sensitivity values are derived from the predetermined signals and are used to determine the at least one character.

49. The method as defined in claim 45 wherein at least one of a numerical value and a numerical range is derived from the predetermined signals, and the at least one character is generated from a combination of the at least one of the numerical value and the numerical range and a predetermined value for a user population.

50. The method as defined in claim 43 wherein the predetermined signals comprise at least one of respiration rate, body temperature, electrocardiogram waveforms, transformed vectorcardiograms waveforms, vectorcardiogram waveforms, heart sounds, accelerometer measurements, physiological measurements, blood pressure, aortic ejection velocity, fingerprint scans, retinal scans, atomic clock data, positional data, voice analysis, data from a microfluidic device, weight, hemoglobin counts, blood oxygen levels, and combinations thereof.

51. The method as defined in claim 43 wherein if the new user is identified, the method further comprises:
    generating a new substantially unique first signature of the new user based on measurements of predetermined signals; and
    replacing the substantially unique first signature with the new substantially unique first signature.

52. The method as defined in claim 43 wherein if the user is identified, the method further comprises:
    updating the substantially unique first signature; and
    saving the updated substantially unique first signature in the electronic device.

53. The method as defined in claim 43 wherein if the user is identified, the method further comprises:
    transforming the second signature to the substantially unique first signature; and
    saving the substantially unique first signature in the electronic device.

* * * * *